United States Patent [19]

Shoenfeld et al.

[11] Patent Number: 5,965,130

[45] Date of Patent: *Oct. 12, 1999

[54] IMMUNOTHERAPEUTIC METHOD OF TREATING CANCEROUS DISEASES BY ADMINISTRATION OF GAMMA GLOBULINS

[75] Inventors: Yehuda Shoenfeld, Ramat-Gan; Pnina Fishman, Herzelya, both of Israel

[73] Assignee: ARP Biomed Ltd., Israel

[ * ] Notice: This patent is subject to a terminal disclaimer.

[21] Appl. No.: 08/487,803

[22] Filed: Jun. 7, 1995

Related U.S. Application Data

[63] Continuation of application No. 08/340,094, Nov. 15, 1994, Pat. No. 5,562,902, and a continuation-in-part of application No. 08/212,361, Mar. 14, 1994, abandoned.

[51] Int. Cl.⁶ .................................................. A61K 39/395
[52] U.S. Cl. ............................................................ 424/130.1
[58] Field of Search ............................................ 424/130.1

[56] References Cited

U.S. PATENT DOCUMENTS 4,699,784   10/1987   Terman et al. .

FOREIGN PATENT DOCUMENTS 0 163 493   12/1985   European Pat. Off. .

OTHER PUBLICATIONS

Apffel, Charles A. et al., "Rejection of Lethal Ascites Tumors After Subcutaneous Inoculation: A Phenomenon of Antigenic Expression?", *J. Nat. Cancer Inst.*, 39, pp. 1129–1139 (1967).

Attard, A.R. et. al., "The Use of Intravenous Immunoglobulin in Malignant Disorders", In *Clinical Applications of Intravenous Immunoglobulin Therapy*, P.L. Yap, ed., Churchill–Livingstone, pp. 203–229 (1992).

Beretta, G. et al., "Chemotherapty Versus Immunotherapy in the Treatment of Human Solidy Tumors", In *Oncogenes to Tumor Antigens*, G. Giraldo et al., eds., Elsevier (1985).

Besa, Emmauel C., "Recent Advances in the Treatment of Chronic Lymphocytic Leukemia: Defining the Role of Intravenous Immunoglobulin", *Seminars in Hematology*, 29, pp. 14–23 (1992).

Brunkhorst, U. et al., "Efficacy of Intravenous Immunoglobulins in Patients with Primary Immunodeficiency Diseases: Inadequacy of Current Dosage Practices and Approaches to the Problem", *Journal of Clinical Immunology*, 2, pp. 15S–21S (1982).

Buckley, Rebecca H., "Long Term Use of Intravenous Immune Globulin in Patients with Primary Immunodeficiency Diseases: Inadequacy of Current Dosage Practices and Approaches to the Problem", *Journal of Clinical Immunology*, 2, pp. 15S–21S (1982).

Buckley, Rebecca H. et al., "The Use of Intravenous Immune Globulin In Immunodeficiency Diseases", *New England Journal of Medicine*, 325, pp. 110–117 (1991).

Cafiero, F. et al., "Prophylaxis of Infection with Intravenous Immunoglobins plus Antibiotic for Patients at Risk for Sepsis Undergoing Surgeryh for Colorectal Cancer: Results of a Randomized, Multicenter Clinical Trial", *Surgery*, 112, pp. 24–31 (1992).

Coon, W.W. et al., "Experiences with Large Infusions of Gamma Globulin", *American Journal of Surgery*, 102, pp. 548–553 (1961).

Dwyer, John M., "Manipulating The Immune System With Immune Globulin", *New England Journal of Medicine*, 326, pp. 107–116 (1992).

Eibl, Martha M. et al., "Intravenous Immunoglobulin: A Review", *Immunodeficiency Reviews*, 1, pp. 1–42 (1989).

Forsberg, John–Gunnar et al., "Growth and Hormonal Responsiveness of Human Endometrial Carcinoma After Heterologous Transplantation to Neonatal Rats", *Journal of the National Cancer Institute*, 43, pp. 191–201 (1969).

Hague, R.A. et al., "Intravenous Immunoglobuln in HIV Infection: Evidence for the Efficacy of Treatment", *Archives of Disease in Childhood*, 64, pp. 1146–1150 (1989).

Hassig, A. "Lucky Strikes and mishaps in the Development and Clinical Use of Human Immunoglobulins", in *Immunomodulation by Intravenous Immunoglobulin*, Rewald E. And A. Morell (eds.), pp. 15–22 (1993).

Glynn, J.P. et al., "An Immunochemotherapeutic system for the Treatment of a Transplanted Moloney Virus–induced Lymphoma in Mice," *Cancer Research*, 29, pp. 515–550 (1969).

Moore, George E. et al., "Experimental and Clinical Adventures with Large Doses of Gamma and Other Globulins as Anticancer Agents", *Surgery*, 41, pp. 972–983 (1957).

Morell, A. et al., Prophylactic and Therapeutic use of Immunoglobulin for Intravenous Admission in Patients with Secondary Immunodeficiencies Associated with Malignancies, *Pediat. Infect. Dis. J.*, 7, pp. S87–S91 (1988).

Mueller, B.M. and R.A. Reisfeld, "Potential of the SCID Mouse as a Host for Human Tumors", *Cancer and Metastasis Reviews*, 10, 193–200 (1991).

Needleman, Samuel W., "Durable Remission of Pure Red Cell Aplasia After Treatment With High–Dose Intravenous Gammaglobulin and Prednisone", *American Journal of Hematology*, 32, pp. 150–152 (1989).

(List continued on next page.)

*Primary Examiner*—Anthony C. Caputa
*Assistant Examiner*—Mark Navarro
*Attorney, Agent, or Firm*—Fish & Neave; Jane A. Massaro

[57] ABSTRACT

This invention provides therapeutic methods for inhibiting tumor metastasis and for treating primary tumors. The methods of this invention do not cause serious side effects and will be effective for a broad spectrum of cancerous diseases. In particular, the invention discloses a novel method comprising administering to a mammal a preparation of intravenous immunoglobulin (IVIG). The IVIG preparation to be administered according to this invention may contain intact immunoglobulin molecules or fragments of immunoglobulins. The preparation is administered parenterally, preferably via intravenous, intracavitary or subcutaneous routes, either as a sole agent or in combination with other agents or methods which are commonly used for cancer treatment.

18 Claims, 1 Drawing Sheet

OTHER PUBLICATIONS

Phillip, M.J. et al., "Effects of Coupled Tumor Specific Antigens (CTSA) on the Growth of Transplanted Tumors in C$_3$ H/HEJ Mice", *Oncology,* 33 pp. 7–11 (1976).

Schlom, J., "Monoclonal Antibodies: They're More and Less Than You Think", In *Molecular Foundations of Oncology,* S. Broder, ed., Williams & Wilkins (1991).

Seidman, Andrew D. et al., "Immune–Mediated Thrombocytopenia Secondary to Suramin", *Cancer,* 71, pp. 851–854 (1993).

Shastri, Kaushik A. et al., "Acquired Factor VIII Inhibitor With Squamous Cell Cancer of the Epiglottis", *Archives of Otolaryngology—Head & Neck Surgery,* 116, pp. 350–353 (1990).

Stiehm, E. Richard et al., "Intravenous Immunoglobulins as Therapeutic Agents", *Annals of Internal Medicine,* 107, pp. 367–382 (1987).

Weeks, Jane C., "Cost Effectiveness of Prophylactic Intravenous Immune Globulin in Chronic Lymphocytic Leukemia", *New England Journal of Medicine,* 325, pp. 81–86 (1991).

Wein, John et al., "Influence of Antisera from Histoincompatible Mice on Electrophoretic Mobility of EL4 Tumor Cells", *Cancer Research,* 27, pp. 1066–1072 (1967).

Xie, X et al., "Comparative Studies Between Nude and SCID Mice on the Growth and Metastatic Behavior of Xenografted Human Tumors", *Clin. Exp. Metastasis,* 10, 201–210 (1992).

The National Institute of Child Health and Human Development Intravenous Immunoglobulin Study Group, "Intravenous Immune Globulin for the Prevention of Bacterial Infections in Children with Symptomatic Human Immunodeficiency Virus Infection", *New England Journal of Medicine,* 325, pp. 73–80 (1991).

NIH Consensus Conference, "Intravenous Immunoglobulin: Prevention and Treatment of Disease", *JAMA,* 264, pp. 3189–3193 (1990).

IMMUNOTHERAPEUTIC METHOD OF TREATING CANCEROUS DISEASES BY ADMINISTRATION OF GAMMA GLOBULINS

This is a continuation of Ser. No. 08/340,094, filed Nov. 15, 1994, now U.S. Pat. No. 5,562,902, which is a continuation-in-part of Ser. No. 08/212,361, filed Mar. 14, 1994, now abandoned.

TECHINICAL FIELD OF THE INVENTION

The present invention relates to cancer therapy and in particular to the administration of gamma globulins to inhibit metastasis and augment treatment of primary cancerous tumors. In accordance with this invention, the treatment of various cancerous diseases is accomplished by administering a preparation containing intact gamma globulins or fragments thereof. The gamma globulin preparation can be administered parenterally, preferably via intravenous, intracavitary or subcutaneous routes, either as a sole drug or in combination with other agents or methods which are commonly used for cancer treatment.

BACKGROUND OF THE INVENTION

The formation of metastases of malignant tumors, initiated from a primary tumor at more or less remote locations of the body, is one of the most serious effects of cancer and one for which a satisfactory treatment protocol is currently unavailable. Cancer tumor metastasis is responsible for most therapeutic failures when the disease is treated, as patients succumb to the multiple tumor growth.

The extent to which metastasis occurs varies with the individual type of tumor. Melanoma, breast cancer, lung cancer, colon cancer and prostate cancer are among the types of cancer that are particularly prone to metastasize. When metastasis takes place, the secondary tumors can form at a variety of sites in the body, with lungs, liver, brain and bone being the more common sites.

The currently available methods of cancer therapy such as surgical therapy, radiotherapy, chemotherapy and other immunobiological methods have either been unsuccessful in preventing metastasis or these methods give rise to serious and undesirable side effects.

In many clinically diagnosed solid tumors (in which the tumor is a localized growth) surgical removal is considered the prime means of treatment. However, many times after surgery and after some delay period, the original tumor is observed to have metastasized so that secondary sites of cancer invasion have spread throughout the body and the patient subsequently dies of the secondary cancer growth. Reports indicate that in individuals with resectable tumors, primary tumor growth or local recurrence is not often the cause of death. Instead, at present, nearly 40% of cancer victims with operable tumors ultimately succumb to metastatic disease following surgery.

Metastasis is a constant occurrence in some tumors. However, many times metastasis is triggered by the surgical operation itself. During the course of surgery malignant cells may become dislodged from the tumor mass and enter the circulatory system thus increasing the chance of metastasis.

Although chemotherapy is widely used in the treatment of cancer, it is a systemic treatment based usually on the prevention of cell proliferation. Accordingly, chemotherapy is a non-specific treatment modality affecting all proliferating cells, including normal cells, leading to undesirable and often serious side effects such as immunosuppression, pancytopenia (growth inhibition of bone marrow cells with anemia, thrombocytopenia and leukopenia), diarrhea, nausea and alopecia (hair loss).

Generally, the existing systemic treatments have, quite often, proven to have little effect on micrometastases already residing in remote organs (lung, liver, bone marrow or brain), and they are not very effective in preventing the dissemination of the tumor to other tissues.

Therefore, the need exists for methods of inhibiting tumor metastasis. In particular, methods which inhibit metastasis without causing serious side effects are much desired.

SUMMARY OF THE INVENTION

The present invention generally solves the problems referred to above by providing therapeutic methods for inhibiting tumor metastasis and for treatment of primary tumors. The methods of this invention do not give rise to serious side effects and will be effective for a broad spectrum of cancerous diseases. In particular, we have disclosed a novel method comprising administering to a mammal a preparation of intravenous immunoglobulins (IVIG). The IVIG preparation to be administered according to this invention may contain intact immunoglobulin molecules or fragments of immunoglobulins. The preparation is administered parenterally, preferably via intravenous, intracavitary or subcutaneous routes, either as a sole agent or in combination with other agents or methods which are commonly used for cancer treatment.

FIG. 1 is a graph demonstrating the effect of IVIG administartion on the survival of melanoma bearing mice. The mice treated with the IVIG had a significantly longer mean-survival time.

DETAILED DESCRIPTION OF THE INVENTION

Definitions

Figure 1:
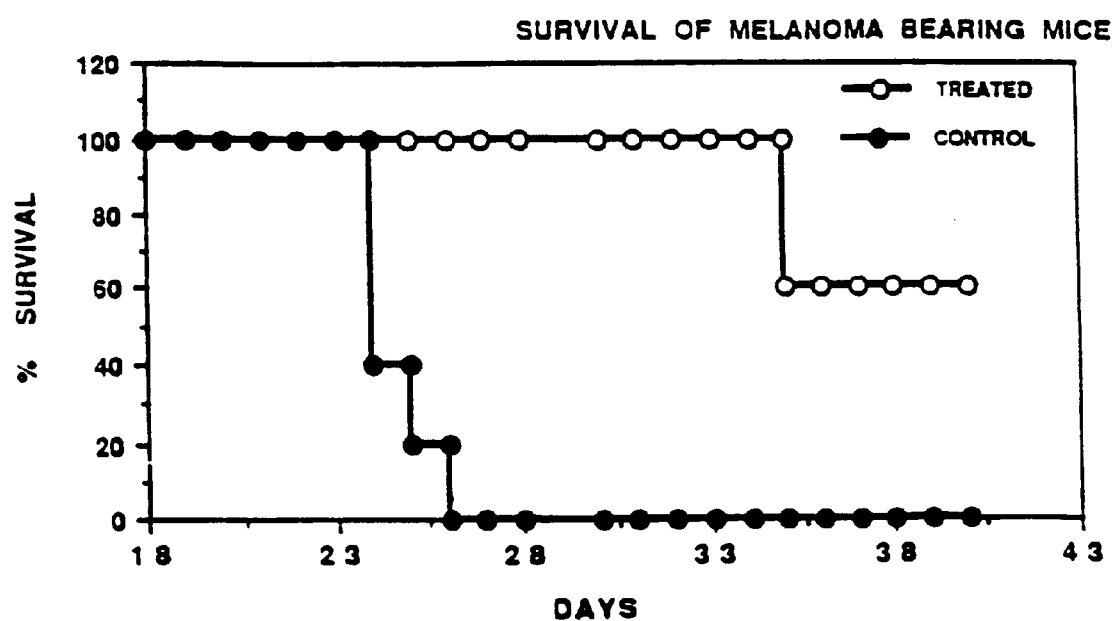

As used herein, "gamma globulin" is the serum globulin fraction that is mainly composed of IgG molecules.

As used herein, "IVIG" or "intravenous immunoglobulins" refers to gamma globulin preparations suitable for intravenous use, such as those IVIG preparations commercially available from several sources.

As used herein, "fragments" of IVIG or gamma globulin are portions of intact immunoglobulins such as Fc, Fab, Fab', $F(ab')_2$ and single chain immunoglobulins.

"Metastasis", as used herein, is defined as the transfer of malignant tumor cells, or neoplasm, via the circulatory or lymphatic systems or via natural body cavities, usually from the primary focus of neoplasia to a distant site in the body, and subsequent development of secondary tumors or colonies in the new location.

As used herein, "metastases" means the secondary tumors or colonies formed as a result of metastasis.

As used herein, "inhibition of metastasis" is defined as preventing or reducing the development of metastases. "Intracavitary administration", as used herein, refers to administering a substance directly into a body cavity of a mammal. Such body cavities include the peritoneal cavity, the pleural cavity and cavities within the central nervous system.

Gammaglobulins suitable for intravenous administration are commonly referred to as Intravenous Immunoglobulins (IVIG) and are commercially available from several sources, for example from Miles Inc. (West Haven, Conn.), N. V. Baxter S.A. (Lessines, Belgium), Sandoz Phama Ltd. (Basle, Switzerland), Instituto Sierovaccinogeno Italiano (Isiven)

(Italy) and Jackson Immunoresearch Laboratories, Inc. (West Grove, Pa.). The commercially available IVIG preparations contain mainly IgG molecules. IVIG has been used in replacement therapy in primary immunodeficiency syndromes and in secondary immunodeficiencies as well as for the prevention and treatment of infectious diseases. Furthermore, IVIG has also been used for immune modulation of patients with autoimmune and immune-complex diseases. See Martha M. Eibl, "Intravenous Immunoglobulin: A Review", *Immunodeficiency Reviews,* 1 (Suppl.), pp. 1–42 (1989).

According to a National Institutes of Health (NIH) Consensus Conference report, the incidence of adverse side effects associated with IVIG use in humans, used at dosage regimens comparable to the ones contemplated by the present invention, is usually less than 5% with most of those reactions being "mild and self-limited." The report adds that "evere reactions occur very infrequently and usually do not contraindicate further IVIG therapy." The NIH report also notes that "[n]either HIV nor hepatitis B infection has been transmitted to recipients of products currently licensed in the United States." NIH Consensus Conference, "Intravenous Immunoglobulin: Prevention and Treatment of Disease", *JAMA,* 264, pp. 3189–3193 (1990).

The present invention stems from our discovery that IVIG as a whole molecule or the F(ab')$_2$ fragment by itself, is extremely useful for the treatment of cancerous diseases in murine models.

The gamma globulin preparations that may be used according to the present invention include commercially available preparations of intact IVIG and preparations of the F(ab')$_2$ fragments of IVIG. Recombinantly produced gamma globulins and their fragments may also be used according to this invention. The use of recombinant single chain antibodies is also envisioned.

The dosage of IVIG and the method of administration will vary with the severity and nature of the particular condition being treated, the duration of treatment, the adjunct therapy used, the age and physical condition of the subject of treatment and like factors within the specific knowledge and expertise of the treating physician. However, single dosages for intravenous and intracavitary administration can typically range from 400 mg to 2 g per kilogram body weight, preferably 2 g/kg (unless otherwise indicated, the unit designated "mg/kg" or "g/kg", as used herein, refers to milligrams or grams per kilogram of body weight). The preferred dosage regimen is 400 mg/kg/day for 5 consecutive days per month or 2 g/kg/day once a month. The IVIG according to the present invention was found to be effective in inhibiting metastasis in animal models when administered by intravenous or intraperitoneal injection and in the dose range of 500–1000 mg/kg/week.

In an other embodiment of this invention, the IVIG preparation is administered via the subcutaneous route. The typical dosage for subcutaneous administration can range from 4 mg to 20 mg per kg body weight. The IVIG according to the present invention was found to be effective in inhibiting metastasis in mice when administered subcutaneously in the dose 200 µg/mouse.

According to the present invention IVIG may be administered as a pharmaceutical composition containing a pharmaceutically acceptable carrier. The carrier must be physiologically tolerable and must be compatible with the active ingredient. Suitable carriers include, sterile water, saline, dextrose, glycerol and the like. In addition, the compositions may contain minor amounts of stabilizing or pH buffering agents and the like. The compositions are conventionally administered through parenteral routes, with intravenous, intracavitary or subcutaneous injection being preferred.

The intravenous immunoglobulins administered according to the present invention act as antimetastatic agents resulting in the reduction of tumor colony number as well as tumor colony size. They can also act prophylactically i.e., to prevent metastasis of tumors. The intravenous immunoglobulins according to this invention may also be used to reduce the size of the primary tumor.

The treatment described in the present invention may also be used either preceding or subsequent to a surgical procedure to remove the primary tumor. Frequently, metastasis of tumor cells will occur as a result of the physical manipulation of the tumor during surgery. However, the use of the treatment described in the present invention in conjunction with surgery will reduce the risk of metastasis and consequently this combination of methods would be a more attractive treatment option for the complete elimination of cancerous tumors.

Similarly, other treatment modalities such as chemotherapy radiation therapy and immunotherapy may also be used in conjunction with the methods of the present invention.

Although not wishing to be bound by any particular theory, we propose that intravenous immunoglobulins inhibit metastasis according to one or more of the following mechanisms.

It is known that tumor metastasis occurs following a detachment of single cancerous cells from the tumor, their migration to adjacent or distal tissues, and their seeding and homing in the new organ. The migration process takes place through adhesion molecules which enable the tumor cells to adhere to the blood vessel wall, to penetrate the blood stream and then to emerge and seed in another tissue. We assume that when whole IVIG or the F(ab')$_2$ fragments of IVIG are applied, they may interfere with the binding of adhesion molecules responsible for the transmission of the tumor cell to and from the blood vessel, and thus prevent the dissemination of the tumor cells to other tissues in the body.

Another possible mechanism is the presence of antibodies or anti-idiotypes in the IVIG mixture which can bind to the tumor cells and induce their lysis in the presence of complement or enhance entrapment of the tumor cells by Fc receptors on the reticuloendothelial system (RES).

An additional possibility is that intravenous immunoglobulins reduce or prevent metastasis by increasing the efficiency of the immune system through inducing the secretion of cytokines such as tumor necrosis factor and interferon gamma.

We are currently conducting experiments to elucidate the exact mechanism by which IVIG preparations exert their observed effects on tumor metastasis.

The effect of IVIG on the dissemination of tumors according to the present invention is demonstrated by the following examples carried out in murine models of melanoma and sarcoma. Additionally, we also present clinical data of a representative human melanoma patient treated with IVIG. These examples are set forth so that this invention may be better understood and are not to be construed as limiting its scope in any manner.

EXAMPLES

MATERIALS AND METHODS

Tumor Cells:

Tumor cell lines from murine origin were used. The murine cell lines included: MCA-105, a methylcholanthrene-induced sarcoma of C57BL/6J origin and B16-F10 melanoma cells (both lines were purchased from American Type Tissue Culture Collection, Rockville, Md.). The cells were routinely maintained in RPMI medium containing 10% fetal calf serum. Twice a week the cells were transferred to a freshly prepared medium.

Experimental Animal Models:

2–3 months old C57BL/6J mice were used during the study. To examine the efficacy of gamma globulin in vivo, 2 types of solid tumors were induced in C57BL/6J mice, e.g. sarcoma (MCA-105) and melanoma (B16-F10). The tumor cells were induced either by intravenous (IV) injection which led to their seeding and lodging in the lung or by intraperitoneal (IP) induction where the cancerous cells developed local lesions in the peritoneum. Some of the mice were sacrificed following 3–5 weeks and examined for metastatic foci in the lungs or spread of tumors in the peritoneum. In another group of mice, survival time was observed. Mice that were injected with tumor cells by IV mode were treated by IV infusion of gamma globulin, whereas in animals in whom the tumor was induced directly in the peritoneum, the gamma globulin preparation was administered through IP injection.

Gamma Globulin Preparations:

Human gamma globulin suitable for intravenous use (IVIG) was obtained from Miles Inc. (Biological Products Division, West Haven, Conn.). A 5% solution (5 gr in 100 ml diluent; Catalogue No. 0640-12) was used for all experiments. Unless otherwise indicated, the volume of IVIG inoculated was 500 µl per animal on each treatment which amounted to 25 mg of gamma globulin per animal. Other preparations used were a whole molecule human gamma globulin or an $F(ab')_2$ fragment both purchased from Jackson Immunoresearch Laboratories, Inc., Pa., (Code Numbers 009-000-003 and 009-000-006 respectively). These latter preparations are different from the one obtained from Miles Inc. in that they are prepared from a donor pool of 30 whereas the Miles preparation is from a donor pool of 3000 or more individuals.

EXAMPLE 1

Effect of Gamma Globulin on the Development of Metastatic Melanoma in C57BL/6J Mice An experimental model for metastatic melanoma was established using the B16-F10 mouse melanoma cell line. The induction of the melanoma was carried out by IV injection of the tumor melanoma cells which are subsequently seeded in the mice lung and form black metastatic foci. Approximately 24 days following tumor inoculation, the mice die.

In the present experiment the mice were injected either with $2 \times 10^5$ tumor cells or with $5 \times 10^5$ cells and were treated intravenously with IVIG (Miles). The mice were sacrificed on day 18 and the efficacy of the treatment was determined by counting the number of the black metastatic foci in the lungs of the animals.

A. Inoculation of mice with $2 \times 10^5$ B16F10 melanoma cells.

20 mice were IV injected with $2 \times 10^5$ melanoma cells and were divided into 4 groups:

(a) Control group, mice inoculated with tumor cells only;

(b) The mice treated with one IV injection of IVIG on day 0 (the day of tumor administration);

(c) The mice treated 2 times, on day 0 and on day 4; and (d) The mice treated 3 times on days 0, 4 and 9.

The mice were sacrificed on day 18 and the number of the metastatic foci in the lungs was evaluated. Table I summarizes the results. One treatment reduced the number of metastatic foci by 80%, while no foci could be detected following two or three treatments.

TABLE I

Reduction in number of metastatic foci in the lung of mice injected with $2 \times 10^5$ B16-F10 melanoma cells and then treated with IVIG

| GROUP | NO. OF FOCI |
| --- | --- |
| Control | 20 ± 4 |
| 1 Treatment | 4 ± 2 |
| 2 Treatments | 0 |
| 3 Treatments | 0 |

Black, metastatic foci are seen in the control group, less foci in the group that was treated with 1 injection of IVIG and none is seen in the lungs that were derived from mice treated by two or three injections of IVIG.

B. Inoculation of mice with $5 \times 10^5$ B16F10 melanoma cells

In order to explore whether IVIG is capable of preventing metastasis when a larger mass of melanoma was involved, the following experiment was conducted. Mice were injected with an increased number of tumor cells ($5 \times 10^5$) and divided into 2 groups:

(a) Control group, inoculated with tumor cells only; and (b) mice treated with 2 IV injection of IVIG on day 0 and on day 8 following tumor inoculation.

On day 18, the mice were sacrificed. Evaluation of the lung metastatic foci revealed a marked decrease in their number in the IVIG treated group. The results are summarized in Table II.

TABLE II

Reduction in number of metastatic foci in the lungs of mice injected with $5 \times 10^5$ B-16 F10 melanoma cells and then treated with IVIG

| GROUP | NO. OF FOCI |
| --- | --- |
| Control | 165 ± 13.4 |
| Two Treatments | 16.3 ± 3.9 |

There is about a 90% reduction in the number of foci in the treated mice when compared to the control group. These results show that IVIG is capable of inhibiting metastatic spread of melanoma even when a larger tumor mass is involved.

C. Effect of Gamma Globulin on the Survival of Melanoma Bearing Mice:

$4 \times 10^5$ B16-F10 cells were injected IV to C57BL/6J mice. The mice were treated from day 0 and every 7th day thereafter with 500 µl Miles IVIG. 24 days following the inoculation of the tumor, the mice from the control group began to die. The results are summarized in FIG. 1. While on day twenty six 100% of the control mice were dead, 100% of the IVIG treated mice were alive. On day 40, 460% of the treated mice were still alive.

EXAMPLE 2

Effect of Gamma Globulin on the Development of MCA-105 sarcoma in C57BL/6J mice:

MCA-105 cells are derived from mice that developed tumors following methyl cholanthrene administration. Two types of experiments were carried out using these cells:

1. Tumor induction by IV infusion:

$2.5 \times 10^5$ MCA-105 cells were injected IV to the tail vein of C57BL/6J mice. One group of mice was treated by IV infusion of IVIG on days 0, 7, and 14 and the mice belonging to the control group were injected on the same days with phosphate buffered saline (PBS).

40 days later the mice were sacrificed and their lungs were evaluated for tumor lesions. The lungs of the control group of mice were much larger than those of the IVIG treated animals and were covered with metastatic foci which appeared as white "blebs".

2. Tumor induction by IP infusion:

$2.5 \times 10^5$ MCA-105 cells were injected IP to C57BL/6J mice. The mice were treated with IVIG from day 0 and every 7th day thereafter till they were sacrificed on day 48. Large tumor foci were observed in the peritoneum in the control group of mice whereas in the treated animals only few small foci were seen.

EXAMPLE 3

Comparison of the Effect of Intact Gamma globulin and F(ab')$_2$ fragment on the development of B-16 melanoma in C57BL/6J mice Mice were IV inoculated with $2.5 \times 10^5$ B16-F10 melanoma cells. The mice were divided into 3 groups:

a) A control group;
b) mice treated with whole molecule IVIG (Jackson Immunoresearch Laboratories Inc.); 5 mg in a volume of 330 μl was injected IV on days 0, 3, 7 and 12; and
c) a group of mice that was treated with 5 mg of F(ab')$_2$ fragment of IVIG (Jackson) in a volume of 500 μl on the same days as in (b).

The mice were sacrificed on day 17 and black metastatic foci were counted in the lung. In the control group 160±18 metastatic foci were counted in comparison to 68±12 in the group treated with the preparation of intact IVIG, and 13±4 foci in the mice treated with the preparation of F(ab')$_2$ fragments of IVIG. This result indicates that both intact IVIG and their F(ab')$_2$ fragments are effective in inhibiting metastases. The observed difference in the effectiveness between the intact IVIG and the F(ab')$_2$ preparation is probably due to the difference in the specific activities of the two solutions used. The difference between the results of Example 1 where the mean number of metastatic foci was 4 when intact IVIG were administered (Table I) and the present example where the mean number of foci was 68 is probably due to the fact that in Example 1, 25 mg of whole IVIG was injected on day 0, whereas in this example only 5 mg was injected on day 0.

EXAMPLE 4

Effect of Gamma Globulin in the Inhibition of Metastasis of Melanoma following Surgical Removal of Primary Tumor C57BL6J mice were injected in the foot pad with $2.5 \times 10^5$ B16F10 melanoma cells. After 21 days the leg in which tumor developed was amputated. On the same day the mice were divided into two groups, one group was treated by intravenous injection of 25 mg IVIG (Sandoz Phama Ltd, Basle, Switzerland; Lot—4.372.256.0) and the other group with phosphate buffered saline (PBS). Ten days later, the mice were examined for signs of tumor development. 60% of the control group developed tumor with a mean size of 3±0.8 cm. 0.8 cm. Those mice died during the first month following amputation. In the IVIG treated group, only 14% of the mice developed tumor (mean size 2.7±1.2 cm). These mice also died during the first month following amputation. The remaining 86% of the IVIG treated mice did not develop tumor and were still alive 45 days following surgery.

EXAMPLE 5

Effect of Low Dose, Subcutaneous Administration of Gamma Globulin in the Inhibition of Melanoma Metastasis C57BL6J mice were injected intravenously with $2.5 \times 10^5$ B16 melanoma cells per mouse. Immediately thereafter, the mice were administered IVIG preparations via the subcutaneous route in the chest area. Four groups of mice (20 mice/group) received 200 μg/mouse of one of the following commercially available IVIG preparations obtained from Baxter (Gammagard S/D 2.5%; Lot-93H23AB12C), Isiven (Isiven V.I. 2.5%; Lot-IS238C6193V), Miles (Gamimmune N 5%; Lot-640N023) and Sandoz (Lot-4.372.256.0). A fifth group of mice receiving intravenous PBS administration acted as the control group. The mice were sacrificed 18 days later and their lungs examined for the presence of metastatic foci. The following table depicts the results.

TABLE III

| GROUP | NO. OF FOCI | % INHIBITION |
|---|---|---|
| Control | 50 | — |
| Baxter | 18.6 | 62.8 |
| Miles | 28.5 | 43.0 |
| Isiven | 18.1 | 63.8 |
| Sandox | 27.9 | 44.2 |

As shown above, low dose, subcutaneous IVIG administration inhibited melanoma metastasis by an average of 53.45% when compared to mice treated with PBS.

EXAMPLE 6

Protocol for Use of Gamma Globulin to Inhibit Metastasis in Human Cancer Patients IVIG preparations are parenterally administered to cancer patients, generally using one of the following dosage regimens for intravenous and intracavitary administration: (1) 400 mg/kg per day for 5 consecutive days per month or (2) 2 g/kg once a month. For subcutaneous use, the IVIG preparation may be administered in the dose of 4 mg/kg per day for 5 consecutive days per month or 20 mg/kg once a month. However, these suggested regimens may be varied according to the patient's age and physical condition, and the severity of disease. The exact protocol will be determined by the treating physician, taking into consideration various factors and circumstances of each patient. Following administration of the gamma globulin preparation, the patient's progress will be monitored according to standard medical procedure. Additionally, the patient will be examined for tumor metastasis or regression.

EXAMPLE 7

Effect of Intravenous Administration of Gamma Globulin to a Representative Melanoma Patient:

A forty two year old male underwent surgery in September 1989 for the wide excision of a malignant melanoma lesion (depth 1.3 mm) on his left thigh. In May 1991, he underwent a hyperthermic perfusion of the leg with cisplatinum because of a local recurrence of the melanoma in a left femoral lymph node. At that time there was no evidence of metastatic disease in the patient. In February 1993, computerized tomography (CT) scans of the chest and abdomen revealed mass lesions in the spleen (one lesion), the liver (five lesions, the largest being 3×3cm) and the lungs (four lesions, the largest being 1.5×1.5cm). Despite the lesions, the patient was asymptomatic. Soon thereafter, a treatment with IVIG was begun. The patient was intravenously administered IVIG (Miles) at a dose of 400 mg/kg/day for 5 consecutive days per month. After five cycles of treatment, all of the spleen and liver metastases disappeared and there was also a slight reduction in the lung lesions. Afterwards, the patient's condition deteriorated with the appearance of new bone and subcutaneous lesions. He continued to receive IVIG with minor reemergence of liver metastases. The patient expired after receiving 12 cycles of IVIG.

As will be appreciated by one of skill in the art, large liver and spleen metastases of melanoma do not regress spontaneously. Furthermore, it is well known that after the detection of such large metastases, the survival time of patients is usually no longer than a few months.

While we have described above specific examples of this invention, it will be apparent to those skilled in the field of cancer therapy that our basic methods may be altered according to need. Therefore, it will be appreciated that the scope of our invention is to be defined by the claims appended hereto rather than by the specific embodiments presented hereinbefore by way of example.

We claim:

1. A method for inhibiting metastasis of a tumor in a mammal which comprises administering to the mammal a preparation of IVIG in an amount of 2 g/kg of body weight per month.

2. The method according to claim 1, wherein the preparation is administered intravenously.

3. A method for inhibiting the growth of a primary tumor in a mammal which comprises administering to the mammal a preparation of IVIG in an amount of 2 g/kg of body weight per month.

4. The method according to claim 3, wherein the preparation is administered intravenously.

5. A method for inhibiting the growth of a primary tumor in a mammal which comprises administering to the mammal a preparation of fragments of IVIG selected from the group consisting of F(ab')$_2$, Fab', Fab and Fc, in an amount effective to inhibit growth of the primary tumor.

6. The method according to claim 5, wherein the preparation is administered intravenously.

7. A method for inhibiting the growth of a primary tumor in a mammal which comprises administering intracavitarily to the mammal a preparation of IVIG or fragments thereof selected from the group consisting of F(ab')$_2$, Fab', Fab and Fc, in an amount effective to inhibit growth of the primary tumor.

8. A method for inhibiting the growth of a primary tumor in a mammal which comprises administering subcutaneously to the mammal a preparation of IVIG or fragments thereof selected from the group consisting of F(ab')$_2$, Fab', Fab and Fc, in an amount effective to inhibit growth of the primary tumor.

9. A method for inhibiting metastasis of a tumor in a mammal which comprises administering to the mammal a preparation of fragments of IVIG selected from the group consisting of F(ab')$_2$, Fab', Fab and Fc, in an amount effective to inhibit metastasis.

10. The method according to claim 9, wherein the preparation is administered intravenously.

11. A method for inhibiting metastasis of a tumor in a mammal which comprises administering intracavitarily to the mammal a preparation of IVIG or fragments thereof selected from the group consisting of F(ab')$_2$, Fab', Fab and Fc, in an amount effective to inhibit metastasis.

12. A method for inhibiting metastasis of a tumor in a mammal which comprises administering subcutaneously to the mammal a preparation of IVIG or fragments thereof selected from the group consisting of F(ab')$_2$, Fab', Fab and Fc, in an amount effective to inhibit metastasis.

13. The method according to claim 8 or 12, wherein the preparation is administered in a dosage range of 4–20 mg/kg of body weight.

14. The method according to any one of claims 1, 2, 9, 10, 11, or 12, wherein the preparation is administered both before and after surgically removing the tumor.

15. The method according to claim 1, 2, 3, 4, 6, 7, 8, 9, 10, 11, or 12, further comprising subjecting the mammal to at least one other treatment modality, prior to, during or after the administration of the preparation.

16. The method according to claim 15, wherein the other treatment modality is selected from the group consisting of chemotherapy, radiation therapy and immunotherapy.

17. The method according to claim 13, further comprising subjecting the mammal to at least one other treatment modality, prior to, during or after the administration of the preparation.

18. The method according to claim 17, wherein the other treatment modality is selected from the group consisting of chemotherapy, radiation therapy and immunotherapy.

* * * * *